United States Patent [19]

Kehrbach et al.

[11] Patent Number: 4,552,877

[45] Date of Patent: Nov. 12, 1985

[54] $N_b$-QUATERNARY DERIVATIVES OF SANDWICINE AND ISOSANDWICINE METHODS AND INTERMEDIATE PRODUCTS IN THE MANUFACTURE OF THEIR DERIVATIVES AND METHODS OF USING SAME AND PHARMACEUTICAL COMPOSITIONS THEREOF

[75] Inventors: Wolfgang Kehrbach, Hanover; Joachim Wegener, Algermissen; Ulrich Kuehl, Hanover; Renke Budden, Hanover; Gerd Buschmann, Hanover, all of Fed. Rep. of Germany

[73] Assignee: Kali-Chemie Pharma GmbH, Hanover, Fed. Rep. of Germany

[21] Appl. No.: 615,756

[22] Filed: May 31, 1984

Related U.S. Application Data

[63] Continuation of Ser. No. 395,649, Jul. 6, 1982, abandoned, which is a continuation of Ser. No. 195,619, Oct. 9, 1980, abandoned.

[30] Foreign Application Priority Data

Oct. 31, 1979 [DE] Fed. Rep. of Germany ....... 2941530

[51] Int. Cl.⁴ ................. A61K 31/435; C07D 455/00; C07D 471/08
[52] U.S. Cl. .................................. 514/239; 514/279; 514/281; 544/125; 546/40; 546/43
[58] Field of Search ................... 546/40, 43; 544/125; 424/248.57, 256; 514/239, 279, 281

[56] References Cited

PUBLICATIONS

Petter et al., "The Antifibrillatory Effect on the Heat of Ajmaline, Bromo-Ajmaline, Quinidine and Novocainamide" (1962).

Volkner et al., "Ueber die Herzwirkung von Ajmalindervaten bei Kanlnchen, Beurteilt an der Veraenderung der QUR-Komplexe" (1982).

*Primary Examiner*—Donald G. Daus
*Assistant Examiner*—Diana G. Rivers
*Attorney, Agent, or Firm*—Schwartz, Jeffery, Schwaab, Mack, Blumenthal & Evans

[57] ABSTRACT

New $N_b$-quaternary 10-bromosandwicine and 10-bromoisosandwicine derivatives are disclosed which exhibit antiarrhythmic properties and adrenolytic properties and which have the formula I

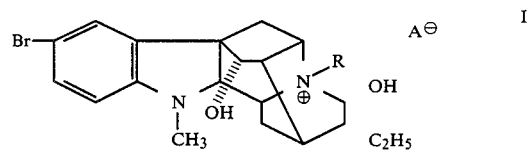

wherein R represents a carbon-attached organic group containing 1 to 10 carbon atoms and $A^\ominus$ represents an acid anion, as well as pharmaceutical formulations thereof and processes and intermediates for their preparation.

8 Claims, 2 Drawing Figures

FIG. I

$N_b$-QUATERNARY DERIVATIVES OF SANDWICINE AND ISOSANDWICINE METHODS AND INTERMEDIATE PRODUCTS IN THE MANUFACTURE OF THEIR DERIVATIVES AND METHODS OF USING SAME AND PHARMACEUTICAL COMPOSITIONS THEREOF

This is a continuation of application Ser. No. 395,649, filed July 6, 1982 which is a continuation of Ser. No. 195,619 filed Oct. 9, 1980, both now abandoned.

BACKGROUND OF THE INVENTION

The invention relates to new 10-brominated $N_b$-quaternary derivatives of sandwicine and isosandwicine, process and intermediate materials for their preparation and pharmaceutical compositions and methods of treatment using same.

Sandwicine is an indole alkaloid from the group of rauwolfia alkaloids. This alkaloid is described in detail by M. Gorman et al, Tetrahedron 1, 328 (1957). It is an isomer of the rauwolfia alkaloid ajmaline. Quaternary salts of ajmaline are known to possess valuable pharmacological properties, in particular, antiarrhythmic properties.

From German Pat. Nos. 11 54 120, 11 96 207 and 16 20 559, $N_b$-quaternary derivatives of ajmaline and isoajmaline are known which exhibit valuable pharmacological activities in particular antiarrhythmic activity. A well known representative of these known quaternary ajmaline derivatives is $N_b$-propyl ajmalinium hydrogen tartrate which is the active ingredient of an antiarrhythmic pharmaceutical composition which is commercially availble under the tradename Neo Gilurytmal, and is used in the treatment of disorders of the coronary and circulatory system.

It is known that quaternary ajmaline derivatives in addition to their desirable pharmacological properties also possess some undesirable side effects, e.g. negative inotropic properties.

From German Offenlegungsschrift No. 26 11 162, $N_b$-quaternary derivatives of sandwicine and isosandwicine are known which possess antiarrhythmic properties.

SUMMARY OF THE INVENTION

It is an object of the present invention to provide new pharmacologically active sandwicine derivatives which exhibit improved pharmacological properties and in particular possess strong cardiac rhythm regulative properties and an increased physiological compatability.

It is a further object of the present invention to provide new antiarrhythmic compounds which are low in side effects, especially low in negative inotropic side effects and low in toxicity.

It is a further object of the present invention to provide new sandwicine derivatives which exhibit adrenolytic properties.

It is a further object of the present invention to provide process for the preparation of such quaternary sandwicine derivatives.

It is still a further object of the present invention to provide pharmaceutical solid or liquid formulations containing such quaternary sandwicine derivatives.

It is a further object of the present invention to provide a method of treatment or prevention of diseases of the coronary and circulary system, especially heart rhythm disorders.

In order to accomplish the foregoing objects according to the present invention there are provied novel $N_b$-quaternary 10-bromosandwicine and 10-bromoisosandwicine compounds of the formula I

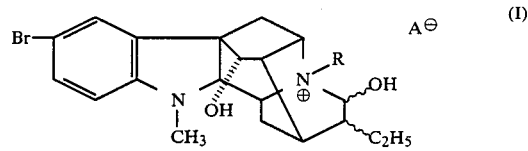

wherein R is a carbon-attached organic residue containing 1 to 10 carbon atoms which may further contain at least one halogen atom or at least one oxygen atom or at least one nitrogen atom or at least one oxygen and one nitrogen atom; and $A^{\ominus}$ is an anion of an organic or inorganic acid.

According to the present invention, there are further provided processes for preparing the compounds of formula (I) and of the intermediate aldehydes of formula IV

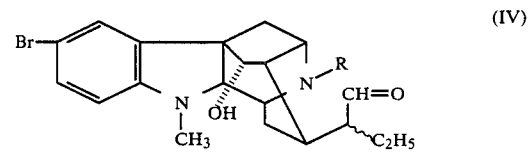

The new compounds of formula I exhibit valuable pharmacological properties, especially antiarrhythmic and adrenolytic properties.

According to the present invention there are further provided pharmaceutical compositions comprising the above-described compounds of formula I and inert diluents.

Further objects, features and advantages of the present invention will become apparent from the detailed description of the invention and the figures of drawings below.

DETAILED DESCRIPTION OF THE INVENTION

Figure 1:
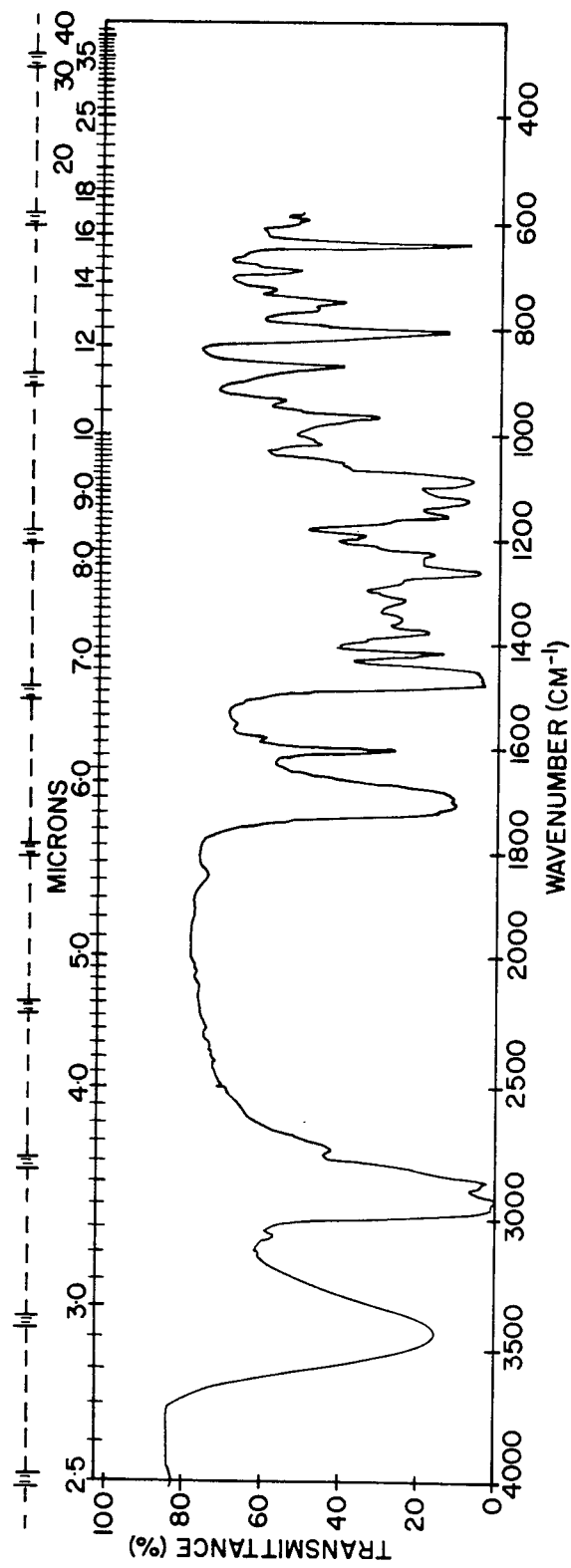
FIG. 1 represents the infrared-spectrum of the aldehyde base derived from $N_b$-hexyl-10-bromosiosandwicine.

Within the formula (I) R may represent a group containing 1 to 10 carbon atoms and having the formula II

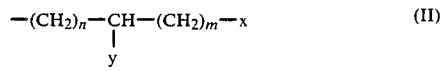

wherein n is 0 or 1; m is 0 or 1; x is hydrogen, hydroxy, straight or branched alkyl which is unsubstituted or is substituted, phenyl which is unsubstituted or is substituted, dialkylamino, pyrrolidino, piperidino or morpholino; and y is hydrogen, hydroxy or methyl or x and y together form a bond with the proviso that when y is hydroxy n is 1 and that when x and y together form a bond n and m each are 1. When x represents alkyl, this alkyl group may be unsubstituted or substituted by hydroxy, alkoxy, halogen or dialkylamino.

When x represents phenyl, this phenyl group may be unsubstituted or substituted by alkyl, alkoxy or halogen.

Most preferably R represents one of the following: methyl, ethyl, allyl, propyl, butyl, 3-methylbutyl, hexyl, decyl, benzyl, 4-fluorobenzyl, 4-methoxybenzyl, 2-hydroxyethyl, 2-hydroxy-2-phenylethyl, 2-diethylaminoethyl, 3-diethylaminopropyl, 2-(1-pyrrolidinyl)ethyl, 2-(1-piperidinyl)ethyl, 2-(4-morpholinyl)ethyl or 2-hydroxy-3-(1-piperidinyl)propyl.

Advantageously, A⊖ represents the anion of a pharmacologically acceptable acid, preferably an anion of tartaric acid, oxalic acid, citric acid, hydrochloric acid or phosphoric acid, most preferably an anion of tartaric acid.

The 10-brominated $N_b$-quaternary sandwicine and isosandwicine compounds can be prepared in the following manner.

Compounds of formula III

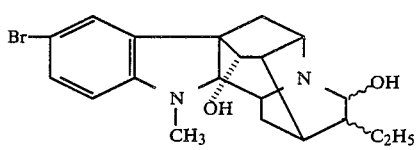

(III)

that is 10-bromosandwicine of formula IIIa

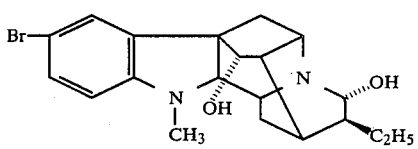

(IIIa)

wherein 21-hydroxy substituent is in α-position and the 20-ethyl substituent is in the β-position or 10-bromoisosandwicine of formula IIIb

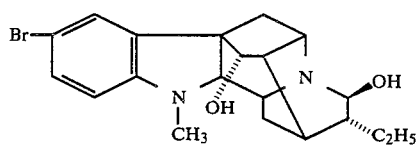

(IIIb)

wherein the 21-hydroxy substituent is in the β-position and the 20-ethyl substituent is in the α-position are alkylated with an alkylating agent of the formula R-Z wherein R is as defined above and Z is halogen or an acid residue of a reactive ester to obtain compounds of formula Ia

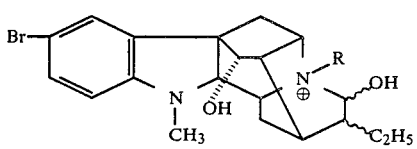

(Ia)

wherein R and Z are as defined above.

The alkylating agent preferably is a compound of formula V

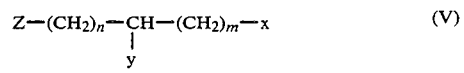

(V)

wherein n, m, x and y are as defined above and Z represents chlorine, bromine, iodine or tosyl. Thus within the process according to the present invention alkylating agents not only include alkyl halides but also the halides and tosylates of optionally substituted alkyl and phenylalkyl groups, as is further demonstrated by the examples below.

The quaternization of the compounds of formula (III) can be performed in any conventional manner. Equimolar amounts of the starting material may be used. Advantageously, an excess of the alkyl halide may be used. It is advisable to effect the quaternizing reaction in the presence of an organic solvent which is inert towards the reacting compounds. Suitable solvents are, for example, acetonitrile, chloroform, dimethylformamide, sulfolane,* dioxane or lower alkyl alcohols, such as for example, methanol and ethanol. Alkylating agents which under the reaction conditions do not react with themselves may also serve as a solvent. The reaction is suitably carried out at elevated temperatures preferably at reflux temperature of the solvent. Yet, in particular, where the solvent has a high boiling point, the reaction may also be carried out at temperatures below the reflux temperature.

* = 2,3,4,5 = tetrahydrothiophen-1,1-dioxide

The quaternary salts of 10-bromoisosandwicine and 10-bromosandwicine which are obtained from the above alkylation may themselves be final products where the anion of the salt is a pharmacologically acceptable anion and the quaternary salt is suitable for the intended galenic formulation.

If a quaternary salt is not suitable for the intended use, e.g. because it is hygroscopic or the anion therein is not pharmacologically acceptable, the quaternary salt of formula I can be transformed into the corresponding open-ring aldehyde base of formula IV

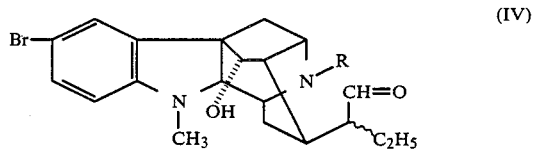

(IV)

wherein R is as defined above by treatment with an alkaline agent. The latter can be subsequently reacted with an acid of the formula H⊕ A⊖ wherein A⊖ is as defined above to form any quaternary salt of formula I.

Suitable alkaline agents for transforming a quaternary salt of formula I into the corresponding aldehyde base include aqueous solutions of alkaline compounds. Particularly suitable alkaline solutions are alkali hydroxide solutions, especially a 10% sodium hydroxide solution, or a solution of sodium hydrogen carbonate or sodium carbonate. It is advisable to effect the reaction in the presence of a suitable extracting solvent. All inert solvents which are not water-miscible are appropriate such as chloroform, methylene chloride, ethyl acetate, diethylether and the like wherein the aldehyde bases are sufficiently soluble.

After distilling off the extracting solvent, advantageously under vacuum, the basic aldehyde bases are recovered in amorphous form.

Finally, the thus prepared aldehyde bases can be reacted with a pharmacologically acceptable acid, e.g. one of the above-cited organic or inorganic acids to form the quaternary salt of formula I. It is not necessary that the aldehyde base is isolated prior to treating it with the acid. The raw dried and clarified organic extract obtained from the alkaline treatment of the quaternary salt of formula Ia can be used as such.

Aldehyde bases of formula IVa

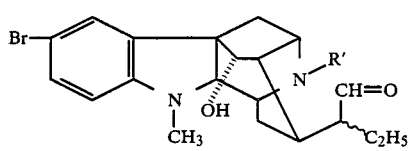

wherein R' is a group of the formula IIa

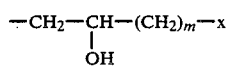

wherein m and x are as defined above may also be obtained directly by alkylating a compound of formula III with an epoxide of formula VI

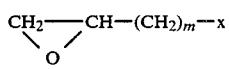

wherein m and x are as defined above.

The aldehyde base can then be treated with an acid $H^\oplus A^\ominus$ to obtain the corresponding quaternary salt of formula I.

Since the ring-open aldehyde base are amorphous, not crystalline, they do not exhibit a definite melting point. Optical rotation values also cannot be used for exact characterization of the compounds, since during the quaternization of bromosandwicine or bromoisosandwicine respectively an isomerization at the carbom atoms in the 20- and 21-position may take place. Independently of whether the starting material is pure bromosandwicine or pure bromoisosandwicine, this isomerization leads to a mixture of the stereoisomer quaternary salts or aldehyde bases. Yet the composition of the mixture varies depending on whether the starting material is bromosandwicine or bromoisosandwicine. The degree of isomerization is depending on the special requirement of the group R and the type of its substitution.

The ratio between the isomers may also vary from one experiment to another in case the reaction conditions are not exactly the same. During the transformation of the aldehyde base into the quaternary salt the ratio between the isomers can be changed further.

Therefore, the ring-open aldehyde bases are most advantageously characterized by the position of the resonance of the aldehyde proton in the 1H-FT-NMR-spectrum and by the occurrence of a carbonyl-bond in the infrared spectrum. The resonance occurs at 9.0-9.6$^\delta$ whereas the carbonyl bond appears at about 1700-1720 cm$^{-1}$.

Figure 2:
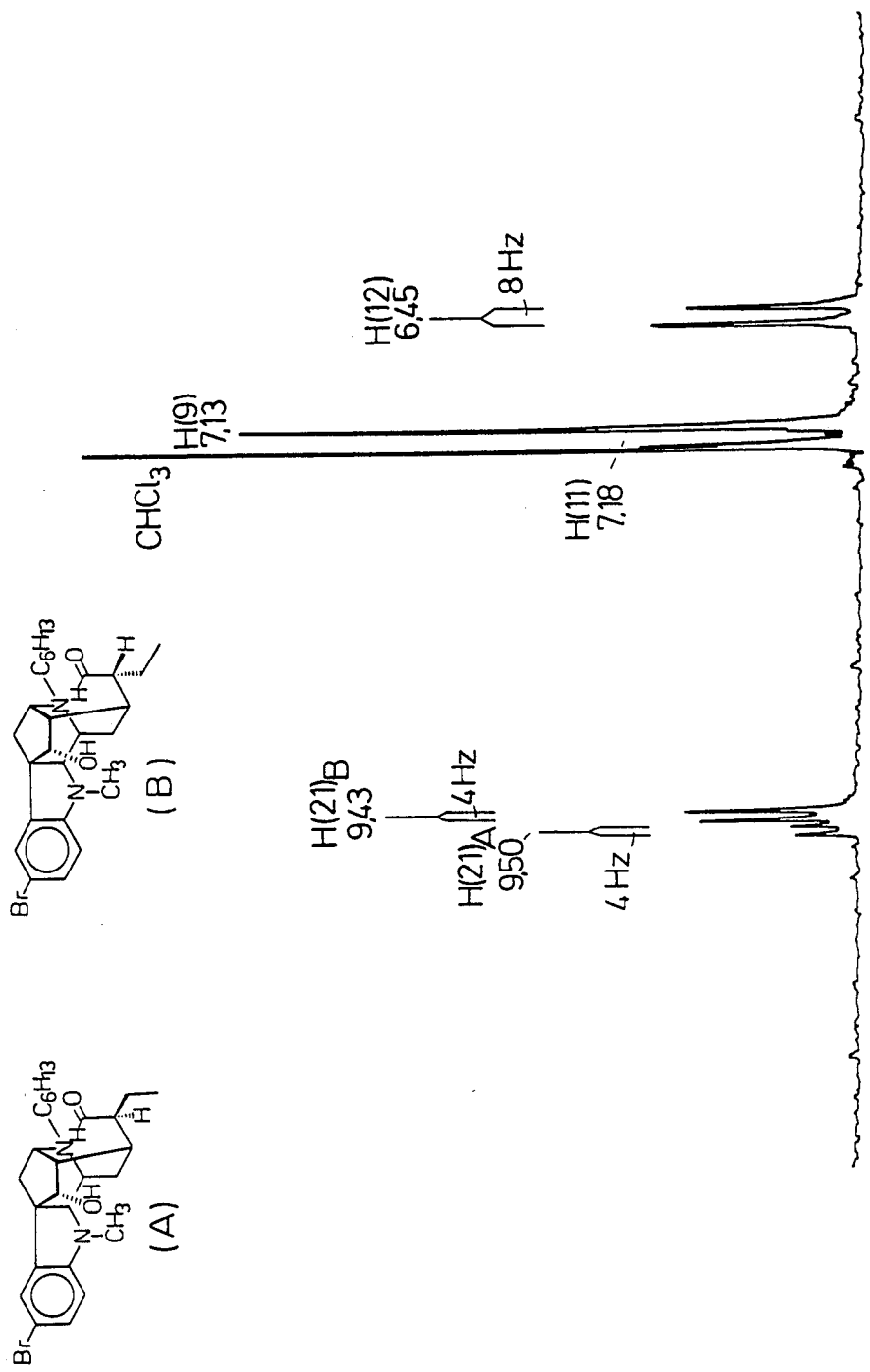
FIG. 2 represents a portion of the 90 MHz 1H-FT-NMR-spectrum of the same compound.

FIGS. 1 and 2 show the infrared spectrum and a portion of the 90 MHz 1H-FT-NMR-spectrum respectively of a representative of aldehyde base, namely the aldehyde base derived from $N_b$-hexyl-10-bromoisosandwicine. In the infrared spectrum the C=O bond is seen at 1710 cm$^{-1}$. In the NMR-spectrum the resonance of the O=CH-aldehyde proton at $C_{21}$ which appears in the low field is characteristic. It is split with a frequency of 4 Hz by coupling with a single adjacent proton at $C_{20}$. The occurrence of two signals is due to the presence of a mixture of two isomer forms, the n-form (signal at 9.50) and the iso-form (signal at 9.43). The ratio between the isomers can be estimated from the respective heights of the peaks.

The isolated aldehyde base, after isolation or in the form of a solution in the extracting solvent is subsequently reacted with a pharmacologically acceptable organic or inorganic acid, preferably tartaric acid, oxalic acid, citric acid, hydrochloric acid or phosphoric acid and thereby is converted into the quaternary compound.

Where in the following, the terms "n-form" or "iso-form" are used, these terms pertain exclusively only to the configuration at the $C_{20}$-position. The 21-hydroxy substituent usually is in the trans-position, yet can also be in the cis-position.

The $N_b$-quaternary compounds of formula (I), according to the present invention, exhibit valuable pharmacological properties and, therefore, are useful in medical treatment. In particular, they are useful in the treatment and prophylaxis of diseases of the coronary and circularly system, e.g. they are useful as antiarrhythmics in the treatment of heart rhythm disorders, since they exhibit adrenolytic and antiarrhythmic activities, as is indicated in standard tests, e.g. measurement of the functional refractory period and the contraction force in the isolated left atria of a guinea pig.

For the above-mentioned uses, the administered doses can vary considerably depending on the type of the compound, the metal, the mode of administration, the treated conditions and the therapy which is desired. Usually satisfactory results are obtained with dosages between 0.05 and 25 mg/kg body weight. These doses can be administered enterally, preferably orally, or parenterally. For example, daily oral doses for larger mammanls can be chosen between 0.5 and 100 mg.

Surprisingly, the new compounds of formula (I) are considerably more active and physiologically better acceptable than the known ajmaline derivatives. Thus, in comparison with known ajmaline derivatives, the effect of the new compounds is similar to that of the ajmaline derivatives at considerably lower dosages. Furthermore, the undesirable negative inotropic effect, which is observed with the ajmaline compounds, is reduced, and at the same time, the new compound of formula (I) exhibit an increased therapeutic range.

According to a further embodiment of the invention, there are provided pharmaceutical compositions containing at least one of the compounds of formula (I). The compounds of formula (I) are stable and storable in aqueous solution, as well as in the solid state. The compositions may take the form of solid or liquid formulations for enteral, preferably oral, or for parenteral administration. Thus, the formulations may be in the form of capsules, tablets, coated tablets, suppositories, emulsions or solutions. These formulations may comprise conventional pharmaceutical carriers, e.g. solids such as starch, lactose, mannit, polyvinyl pyrrolidone or liquids such as sterile water, pharmaceutically acceptable alcohols or fatty oils, and may further comprise pharmaceutical adjuvants, e.g. binders or lubricants for tabletting, stabilizing, flavoring or emulsifying.

The superior properties of the compounds according to the present invention is seen from the pharmacological data given in the table below wherein the pharmacological properties of the representatives of the compounds of the present invention are compared with those of the known $N_b$-propylajmalinium hydrogen tartrate (trademark Neo-Gilurytmal ®).

The following data are given in the Table:

The acute toxicity of the compounds is determined in male NMRI-mice (body weight range 18–22 g) after oral (p.o) and intraperitonal (i.p.) administration. The $LD_{50}$ is defined as that dose in μmole/kg which causes a 50% mortality rate of the test animals on the 7th day after application. The calculation of the $LD_{50}$ is carried out by probitanalysis (see L. Cavalli-Sforza, *Grundbegriffe der Biometrie,* Gustav Fischer Verlag, Stuttgart, (1964)).

The minimum symptom dose is determined in male NMRI-mice (body weight range 18–22 g) according to the procedure of Campbell and Richter (see D.E.S. Campbell and W. Richter, *Acta Pharmacol Toxicol,* 25 (1967), pp 345–363). The minimum symptom dose is defined as that dose in μmol/kg which after i.p. administration causes changes in behavior in 2 out of 3 mice. The minimum symptom dose is a measure for evaluating undesirable side effects.

The prolongation of the functional refractory period (FRP) and the contraction force (CF) in the isolated left atria of female guinea pigs (albino Pirbright-white guinea pigs, body weight 300–400 g) are determined according to the double stimulus method of Govier (see W.C. Govier, *J. Pharmakol. Exp. Ther.* 148 (1965) pp 100–105). The concentrations which are given in the table below are the concentrations in μmol/l which 18 minutes after application leads to a prolongation of the functional refractory period to 125% or respectively to a reduction of the contraction force to 75% of the starting value. Furthermore, the ratio between contraction force-reducing dose and functional refractory period-prolonging dose is given. This ratio is an indication of the therapeutic range of the antiarrhythmic effect on the isolate organ (see K. Gref, *Verh. Dtsch. Ges. Kreislaufforsch.* 35 (1969) pp 88–97).

Since some of the data are given in μmol/kg, the calculated molecular weight (MW) of the test compounds is also given in the following table.

Preparation of 10-bromosandwicine 26.6 g of sandwicine are dissolved in 2 liters of a mixture of tetrahydrofuran and methylene chloride in a volume to volume ratio of 4:1. 33 g of 2,4,4,6-tetrabromo-2,5-cyclohexadien-1-one are added portionwise under stirring at a temperature of −5° C. After the last portion has been added, the mixture is agitated for another 30 minutes at a temperature of −5° to −10° C., then the mixture is warmed up to room temperature, additional methylene chloride is added and the mixture is washed twice with 2 n-sodium hydroxide solution and subsequently twice with water. The organic phase is evaporated, the residue is dissolved in 500 ml of methanol. Water is added dropwise and slowly to the methanolic solution until the precipitation of the 10-bromosandwicine is complete. The product is filtered off by suction, then washed with water and subsequent with cold acetone and is dried.

Yield: 30.1 g (91%).

Melting Point: 204° C., pure n-form.

By acidifying the aqueous alkaline extracts, 2,4,6-tribromophenol could be recovered which after recrystallization from petrolether can again be used for the preparation of 2,4,4,6-tetrabromo-2,5-cyclohexadien-1-one.

Preparation of 10-bromoisosandwicine 15 g of bromosandwicine and 20 g of potassium hydroxide are dissolved in 700 ml of methanol and are heated to reflux for 8 hours. After diluting with 400 ml of water the mixture is extracted three times with methylene chloride. The organic phase is dried, evaporated and the product is crystallized from methanol.

Yield: 10.5 g (70%).

Melting Point: 173°–175° C., pure iso-form.

The mixture of 10-bromosandwicine and a small amount of 10-bromoisosandwicine which remains in the mother liquor can again be isomerized.

The following examples further describe the present invention yet without limiting it.

The quaternary salts which are prepared according to the examples below are transformed into the corresponding free aldehyde bases and the latter are subsequently reacted with L(+)-tartaric acid into the corresponding hydrogen tartrate. Aldehyde bases which contain an alkyl substitute which is free from additional nitrogen are reacted with equimolar amount of tartaric acid. Aldehyde bases which contain a nitrogen-containing alkyl group are reacted with twice the molar amount of tartaric acid.

TABLE

| Example | Test Compound R | MW | $LD_{50}$ i.p μmol/kg | $LD_{50}$ p.o μmol/kg | Min. Symptom-dose μmol/kg | Isolated Guinea Pig Atria CF μmol/l | FRP μmol/l | CF/FRP |
|---|---|---|---|---|---|---|---|---|
| Comparative Compound n-C3H7 (Neo-Gilurytmal) | | 519 | 41 | 65 | 12 | 0.26 | 1.8 | 0.15 |
| (1.b) | —CH3 | 569 | 325 | 1910 | 11 | 20.2 | 3.2 | 6.4 |
| (2.b) | n-C3H7 | 598 | 101 | 1133 | 42 | 4.7 | 1.4 | 3.3 |
| (4.b) | n-C6H13 | 640 | 112 | >2300 | 39 | 2.0 | 4.3 | 0.5 |
| (8) | 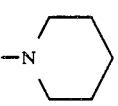 —CH2—CHOH—CH2—N⟩ | 847 | 169 | 1190 | 59 | 3.4 | 8.3 | 0.4 |
| (12.b) | n-C3H7 | 598 | 118 | 566 | 10 | 6.5 | 1.8 | 3.6 |

The starting materials 10-bromosandwicine and 10-bromoisosandwicine are prepared as follows:

Examples 1 to 10 pertain to alkylation of 10-bromosandwicine.

EXAMPLE 1a $N_b$-methyl-10-bromosandwicine iodide 12 g of 10-bromosandwicine and 13 ml of methyl iodide are heated in 500 ml of acetonitrile under reflux for 8 hours. The resulting precipitate is filtered off and is washed with ethyl acetate.

Yield: 9.5 g (59%).
Melting Point: 240°–242° C., pure n-form.

EXAMPLE 1b $N_b$-methyl-10-bromosandwicinium hydrogen tartrate

Diluted sodium carbonate solution is added to 8.7 g of $N_b$-methyl-10-bromosandwicinium iodide and the mixture is extracted with ethyl acetate. A solution of 2.4 g of L(+)-tartaric acid and acetone is added dropwise to the organic extract. The precipitated product is filtered off and washed with ethyl acetate.

Yield: 8.0 g (52%).
Melting Point: 166°–170° C., pure n-form.

EXAMPLE 2a $N_b$-n-propyl-10-bromosandwicinium iodide 10-bromosandwicine is alkylated with n-propyl iodide in a process analogous to Example 1a.

Yield: 67%.
Melting Point: 270° C. (decomposing), pure n-form.

EXAMPLE 2b $N_b$-n-propyl-10-bromosandwicinium hydrogen tartrate

Transformation of the $N_b$-n-propyl-10-bromosandwicinium iodide into the hydrogen tartrate is carried out in a process analogous to Example 1b.

Yield: 57%.
Melting Point: 153°–155° C., pure n-form.

EXAMPLE 3

$N_b$-allyl-10-bromosandwicinium bromide 1 g of 10-bromosandwicine and 1 ml of allyl bromide are dissolved in 30 ml of acetonitrile and the solution is refluxed for 8 hours. The precipitated $N_b$-allyl-10-bromosandwicinium bromide is filtered off under suction, washed with acetone and dried.

Yield: 1.3 g (100%).
Melting Point: 263° C. (decomposing), pure n-form.

EXAMPLE 4a $N_b$-n-hexyl-10-bromosandwicinium iodide 10-bromosandwicine is alkylated with n-hexyl iodide in a process analogous to Example 1a.

Yield: 67%.
Melting Point: 224°–227° C., pure n-form.

EXAMPLE 4b $N_b$-n-hexyl-10-bromosandwicinium hydrogen tartrate

The transformation of the iodide into the hydrogen tartrate is carried out in a process analogous to Example 1b.

Yield: 38%.
Melting Point: 134° C., pure n-form.

EXAMPLE 5

$N_b$-decyl-10-bromoisosandwicinium bromide 1 g of 10-bromosandwicine and 1 ml of 1-bromodecane are dissolved in 15 ml of ethanol and the solution is heated under reflux for 48 hours. The precipitated $N_b$-decyl-10-bromosandwicinium bromide is filtered off under suction, washed with cold ethanol and dried.

Yield: 0.6 g (39%).
Melting Point: 258° C.
n-form:iso-form 3:7.

EXAMPLE 6

$N_b$-(3-methylbutyl)-bromosandwicinium iodide 1 g of 10-bromosandwicine and 1 ml of 1-iodo-3-methylbutane are dissolved in 15 ml of ethanol and are heated under reflux for 24 hours. After cooling, ether is added and the precipitated $N_b$-(3-methylbutyl)-10-bromosandwicinium iodide is filtered off, washed with ether and dried.

Yield: 0.5 g (34%).
Melting Point: 266° C. (decomposing).

EXAMPLE 7

$N_b$-benzyl-10-bromosandwicinium bromide 1 g of 10-bromosandwicine and 1 ml of benzyl bromide are dissolved in 35 ml of acetonitrile and are heated under reflux for 8 hours. The precipitated $N_b$-benzyl-10-bromosandwicinium bromide is filtered off, washed with cold acetone and dried.

Yield: 1 g (70%).
Melting Point: 242° C.
n-form:iso-form 6:4.

EXAMPLE 8

$N_b$-[2-hydroxy-3-(1-piperidinyl)propyl]-10-bromosandwicinium bishydrogen tartrate.

10 g of 10-bromosandwicine and 3.7 g 3-piperidino-1,2-epoxypropane are dissolved in 75 ml of ethanol and are agitated at a temperature of 75° C. After 8 hours, an additional 1 g of 3-piperidino-1,2-epoxypropane is added and the solution is agitated for another 8 hours at 75° C. The solution is then evaporated to dryness under vacuum and the residue is redissolved in about 100 ml of acetone. The resulting solution is added dropwise to a solution of 3.9 g of L(+)-tartaric acid in 250 ml of acetone which is cooled by means of ice. The precipitated bishydrogen tartrate is filtered off and washed with acetone and ether. The bishydrogen tartrate is treated with sodium carbonate solution whereby the free aldehyde base is liberated. The latter is extracted with ether and is again reacted with L(+)-tartaric acid to precipitate the bishydrogen tartrate.

Yield: 9.4 g (45%).
Melting Point: 135° C.

EXAMPLE 9

$N_b$-(2-hydroxy-2-phenylethyl)-10-bromosandwicinium hydrogen tartrate 1 g of 10-bromosandwicine and 0.4 ml of epoxy styrene are dissolved in 15 ml of ethanol and are heated to a temperature of 75° C. for a period of 7 hours. After the addition of an additional 0.3 ml of epoxy styrene the solution is heated to 75° C. for another 8 hours followed by evaporation. Methanol is added to the residue, 0.32 g of L(+)-tartaric acid are added and the reaction mixture is added dropwise slowly into 80 ml of ethyl acetate. The precipitated hydrogen tartrate is filtered off under suction, washed with ethyl acetate and dried.
Yield: 1.5 g (90%).
Melting Point: 139° C.

EXAMPLE 10

$N_b$-(2-hydroxyethyl)-10-bromoisosandwicinium hydrogen tartrate 2 g of 10-bromosandwicine and 7 ml of chloroethanol are dissolved in 10 ml of sulfolane and the reaction mixture is agitated at a temperature of 80° C. under nitrogen for a period of 15 hours. 6-n-hydrochloric acid is added, the reaction mixture is extracted with ethyl acetate. Sodium carbonate solution is added to the aqueous phase to achieve an alkaline medium and the alkaline mixture is repeatedly extracted with ethyl acetate. The organic phase is dried and a solution of 0.7 g of L(+)-tartaric acid in acetone is added dropwise. The precipitated hydrogen tartrate is filtered off under suction, washed with ethyl acetate and dried.
Yield: 1.9 g (64%).
Melting Point: 119° C., pure iso-form.

EXAMPLES 11 TO 14

Alkylation of 10-bromoisosandwicine.

EXAMPLE 11

$N_b$-methyl-10-bromoisosandwicinium iodide

The compound is prepared by reacting 10-bromoisosandwicine with methyl iodide according to the method of Example 1a with the difference that additional product is recovered from the mother liquor by evaporating the mother liquor and treating the residue with a small amount of methylene chloride whereby additional product crystallizes.
Yield: 97%.
Melting Point: 200° C., pure iso-form.

EXAMPLE 12a $N_b$-n-propyl-10-bromoisosandwicinium iodide 10-bromoisosandwicine is reacted with propyl iodide in a process analogous to Example 1a.
Yield: 87%.
Melting Point: 265° C. (decomposing), pure iso-form.

EXAMPLE 12b $N_b$-n-propyl-10-bromoisosandwicinium hydrogen tartrate 12 g of $N_b$-n-propyl-10-bromoisosandwicinium iodide are added to 300 ml of diluted sodium carbonate solution. The mixture is extracted three times with methylene chloride. The organic phase is dried, largely evaporated and dissolved in 600 ml of ethyl acetate. A concentrated solution of 3.1 g of L(+)-tartaric acid in acetone is added dropwise to that solution. The precipitated hydrogen tartrate is filtered off and washed with ethyl acetate.
Yield: 81%.
Melting Point: 149°–151° C., pure iso-form.

EXAMPLE 12c $N_b$-n-propyl-10-bromoisosandwicinium dihydrogen citrate 1.2 g of $N_b$-n-propyl-10-bromoisosandwicinium iodide are added to 50 ml of diluted sodium carbonate solution and the mixture is extracted twice with 50 ml of ethyl acetate each. A solution of 0.44 g of citric acid-1-hydrate in 3 ml of acetone which has been diluted with a small amount of ethyl acetate is added to the above organic solution and the solution is evaporated to dryness.
Yield: 1.3 g (100%).
Melting Point: 125° C.
n-form:iso-form about 1:4.

EXAMPLE 13

$N_b$-n-hexyl-10-bromoisosandwicinium iodide 10-bromoisosandwicine is reacted with hexyl iodide according to the method of Example 1a with the difference that the entire reaction solution is partially evaporated and a small amount of methylene chloride is added whereby the product precipitates.
Yield: 90%
Melting Point: 245°–246° C.
n-form:iso-form about 1:3.

EXAMPLE 14

$N_b$-(2-morpholinoethyl)-10-bromoisosandwicinium chloride 1.5 g of 10-bromoisosandwicine and 0.8 g of N-(2-chloroethyl)morpholine are dissolved in 12 ml of ethanol and the solution is heated under reflux for 14 hours. The precipitated product is filtered off under suction, washed with methylene chloride and dried.
Yield: 1.5 g (73%).
Melting Point: 257° C., pure iso-form.

EXAMPLE 15

Tablets containing $N_b$-propyl-10-bromosandwicinium hydrogen tartrate as active ingredient.

| Composition: | |
|---|---|
| Active Ingredients | 15 parts |
| Lactose.H$_2$O | 105 parts |
| Corn Starch | 58 parts |
| Aerosil 200* | 0.5 parts |
| Polyvinyl Pyrrolidone (Tradename Kollidon 25) | 10 parts |
| Aerosil 200 | 0.2 parts |
| Magnesium stearate | 1.3 parts |
| Total | 190 parts |

*Aerosil 200 is a tradename for a highly dispersed silicium dioxide.

Preparation:
The active ingredient is slowly mixed with lactose, corn starch and aerosil 200 (highly dispersed silicium dioxide). The resulting mixture is moistened with a 40% aqueous solution of the polyvinyl pyrrolidone in a mixer (Diosna-mixer) and is granulated. The moist material is pressed through a 2 mm mesh size sieve, is dried on shelves at a temperature of 40° C. and subsequently is pressed through a 1.6 mm mesh size sieve. The resulting granulate is mixed with highly dispersed silicium dioxide and magnesium stearate in a cubic mixture and the resulting mixture is pressed into tablets having a total weight of 190 mg, so that each tablet contains 15 mg of the active ingredient.

EXAMPLE 16

Capsules containing $N_b$-propyl-10-bromosandwicinium hydrogen tartrate as active ingredient.

| Composition: | |
|---|---|
| Active ingredient | 15 parts |
| Granulated lactose | 69.5 parts |
| Starch (tradename STA-Rx 1500) | 10 parts |
| Aerosil 200 | 0.5 parts |
| Magnesium stearate | 1.0 parts |
| Total | 96 parts |

Preparation:

The active ingredient is mixed with the starch in a mixer. The granulated lactose (tradename Tabletosa) is added and mixed therewith. The Aerosil 200 (highly dispersed silicium dioxide) and magnesium stearate are passed through a 0.2 mm mesh size sieve and are added to the mixture one subsequent to the other.

By means of an automatically operated capsule filling and closing machine, the powderous material is filled into hard gelatin capsules size No. 4. Each capsule contains an average of 96 mg of the powderous mixture corresponding to 15 mg of active ingredient.

EXAMPLE 17

Tablets containing $N_b$-methyl-10-bromosandwicinium hydrogen tartrate as active ingredient.

| Composition: | |
|---|---|
| Active ingredient | 15 parts |
| Lactose-H$_2$O | 105 parts |
| Corn Starch | 58 parts |
| Aerosil 200 | 0.5 parts |
| Polyvinylpyrrolidone | 10 parts |
| Aerosil 200 | 0.2 parts |
| Magnesium stearate | 1.3 parts |
| Total | 190 parts |

Preparation:

The active ingredient is slowly mixed with lactose, corn starch and Aerosil 200 (highly dispersed silicium dioxide). The resulting mixture is moistened with an aqueous 40% solution of the polyvinylpyrrolidone in a pharmaceutical mixer (Diosna-mixer) and is granulated. The moist material is passed through a 2 mm mesh size sieve, dried on shelves at a temperature of 40° C. and subsequently is passed through a 1.6 mm mesh size sieve. The resulting granulate is mixed with highly dispersed silicium dioxide and magnesium stearate in a cubic mixture and the mixture is pressed into tablets having a total weight of 190 mg, so that each tablet contains 15 mg of the active ingredient.

EXAMPLE 18

Capsules containing $N_b$-methyl-10-bromosandwicinium hydrogen tartrate as active ingredient.

| Composition: | |
|---|---|
| Active ingredient | 15 parts |
| Granulated lactose | 69.5 parts |
| Starch | 10 parts |
| Aerosil 200 | 0.5 parts |
| Magnesium stearate | 1.0 parts |
| Total | 96 parts |

Preparation:

The active ingredient is mixed with the starch in a suitable mixture. Granulated lactose is added and mixed therewith. The Aerosil 200 (highly dispersed silicium dioxide) and the magnesium stearate each are passed through a 0.2 mm mesh size sieve and are added to the mixture one after another.

In an automatically operated capsule filling and closing machine the powderous material is filled into hard gelatin capsules size No. 4. Each capsule contains an average of 96 mg of the powderous mixture corresponding to 15 mg of the active ingredient.

What is claimed is:

1. A $N_b$-quaternary 10-bromosandwicine and 10-bromoisosandwicine compound of the formula I

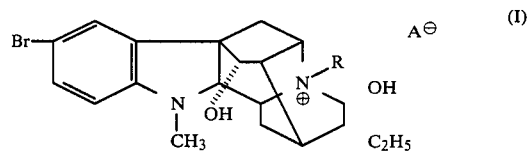

wherein R is a carbon-attached organic residue containing 1 to 10 carbon atoms and having the formula II

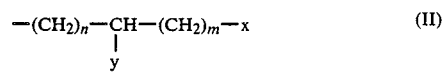

wherein n is 0 or 1; m is 0 or 1; x is hydrogen, hydroxy, straight or branched alkyl which is unsubstituted or is substituted by hydroxy, alkoxy, halogen or dialkylamino, phenyl which is unsubstituted or is substituted by alkyl, alkoxy or halogen, dialkylamino, pyrrolidino, piperidino or morpholino; and y is hydrogen, hydroxy or methyl or x and y together form a bond with the proviso that when y is hydroxy n is 1 and that when x and y together form a bond n and m each are 1 and $A^{\ominus}$ is an anion of a pharmacologically acceptable organic or inorganic acid.

2. The compound as defined in claim 1 wherein R is methyl, ethyl, allyl, propyl, butyl, 3-methylbutyl, hexyl, decyl, benzyl, 4-fluorobenzyl, 4-methoxybenzyl, 2-hydroxyethyl, 2-hydroxyl-2-phenylethyl, 2-diethylaminoethyl, 3-diethylaminopropyl, 2-(1-pyrrolidinyl)ethyl, 2-(1-piperidinyl)ethyl, 2-(4-morpholinyl)ethyl or 2-hydroxy-3-(1-piperidinyl)propyl.

3. The compound as defined in claim 1 wherein $A^{\ominus}$ is an anion of tartaric acid, oxalic acid, citric acid, hydrochloric acid or phosphoric acid.

4. The compound as defined in claim 3 wherein $A^{\ominus}$ is an anion of tartaric acid.

5. A compound of formula IV

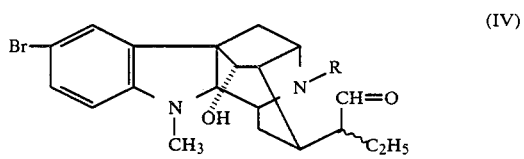

wherein R is a carbon-attached organic residue containing 1 to 10 carbon atoms and having the formula II

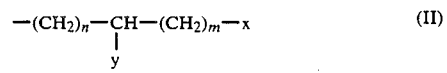

wherein n is 0 or 1; m is 0 or 1; x is hydrogen, hydroxy, straight or branched alkyl which is unsubstituted or is substituted by hydroxy, alkoxy, halogen or dialkylamino, phenyl which is unsubstituted or is substituted by alkyl, alkoxy or halogen, dialkylamino, pyrrolidino, piperidino or morpholino; and y is hydrogen, hydroxy or methyl or x and y together form a bond with the proviso that when y is hydroxy n is 1 and that when x and y together form a bond, n and m each are 1.

6. The compound as defined in claim 5 wherein R is methyl, ethyl, allyl, propyl, butyl, 3-methylbutyl, hexyl, decyl, benzyl, 4-fluorobenzyl, 4-methoxybenzyl, 2-hydroxyethyl, 2-hydroxyl-2-phenylethyl, 2-diethylaminoethyl, 3-diethylaminopropyl, 2-(1-pyrrolidinyl)ethyl, 2-(1-piperidinyl)ethyl, 2-(4-morpholinyl)ethyl or 2-hydroxy-3-(1-piperidinyl)propyl.

7. A pharmaceutical composition comprising a cardiac rhythm regulative effective amount of a compound as defined in claim 1 and an inert pharmaceutical carrier.

8. A method of treating heart rhythm disorders in larger mammals which comprises administering to a larger mammal an effective amount of a compound as defined in claim 1.

* * * * *